(12) United States Patent
Barnell

(10) Patent No.: US 10,639,123 B2
(45) Date of Patent: May 5, 2020

(54) BIOMATTER CAPTURE MECHANISM AND METHOD

(71) Applicant: Medtronic Vascular, Inc., Santa Rosa, CA (US)

(72) Inventor: Jeffrey Barnell, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 511 days.

(21) Appl. No.: 15/277,537

(22) Filed: Sep. 27, 2016

(65) Prior Publication Data

US 2018/0008366 A1 Jan. 11, 2018

Related U.S. Application Data

(60) Provisional application No. 62/359,049, filed on Jul. 6, 2016.

(51) Int. Cl.
*B65D 1/34* (2006.01)
*A61B 50/36* (2016.01)
(Continued)

(52) U.S. Cl.
CPC ........ *A61B 50/36* (2016.02); *A61B 17/00234* (2013.01); *A61B 50/33* (2016.02); *A61F 2/0095* (2013.01); *A61F 2/95* (2013.01); *A61M 25/002* (2013.01); *B65D 1/34* (2013.01); *B65D 25/10* (2013.01); *B65D 25/105* (2013.01); *B65D 43/0202* (2013.01);
(Continued)

(58) Field of Classification Search
CPC ......... A61B 50/30; A61B 50/20; A61B 50/33; A61B 17/00234; A61B 50/36; A61B 2050/314; B65D 1/34; B65D 25/105; A61M 25/002

USPC ................................ 206/364, 438, 370, 363
See application file for complete search history.

(56) References Cited

U.S. PATENT DOCUMENTS 4,106,621 A * 8/1978 Sorenson ............... A61M 5/002
206/365
5,133,454 A * 7/1992 Hammer ............... A61M 5/002
206/364
(Continued)

FOREIGN PATENT DOCUMENTS

CA 907570 8/1972
EP 2106821 A1 10/2009
(Continued)

OTHER PUBLICATIONS

PCT International Search Report corresponding to International Application No. PCT/US2017/040589, dated Sep. 27, 2017, 6 pages.
(Continued)

*Primary Examiner* — Steven A. Reynolds

(57) ABSTRACT

In accordance with one embodiment, a method of capturing biomatter includes placing a device comprising the biomatter within an extension tube, the extension tube being coupled to a tray. A fold is created in the extension tube sealing the extension tube and the biomatter contained therein. The extension tube is secured to the tray to maintain the fold. The assembly is discarded, e.g., into a bio-waste disposal bag in a bio-waste container. The fold is a smooth fold, in contrast to a sharp tip, thus minimizing the possibility of puncture of the bio-waste disposal bag.

17 Claims, 11 Drawing Sheets

(51) Int. Cl.
- *B65D 25/10* (2006.01)
- *A61B 50/33* (2016.01)
- *A61B 17/00* (2006.01)
- *A61F 2/95* (2013.01)
- *A61F 2/00* (2006.01)
- *A61M 25/00* (2006.01)
- *B65D 43/02* (2006.01)
- *A61L 2/20* (2006.01)
- *A61B 50/30* (2016.01)

(52) U.S. Cl.
CPC ............. *A61B 2017/00362* (2013.01); *A61B 2050/314* (2016.02); *A61L 2/206* (2013.01)

(56) References Cited

U.S. PATENT DOCUMENTS

| | | | | |
|---|---|---|---|---|
| 5,203,459 | A * | 4/1993 | Wade | A47G 21/004 206/572 |
| 5,228,782 | A * | 7/1993 | Imer | B65D 75/5822 383/200 |
| 5,842,567 | A * | 12/1998 | Rowe | A61B 50/3001 206/364 |
| 6,428,515 | B1 | 8/2002 | Bierman et al. | |
| 7,028,862 | B2 * | 4/2006 | Poynter | A61J 1/00 222/209 |
| 7,261,205 | B2 * | 8/2007 | Cervantes | A61F 2/0095 206/363 |
| 7,850,006 | B2 * | 12/2010 | Uchiyama | A61B 1/00144 206/350 |
| 8,381,941 | B2 * | 2/2013 | Barton | B65D 75/366 206/484 |
| 9,022,212 | B2 * | 5/2015 | Spaargaren | A61M 25/002 206/364 |
| 9,187,225 | B2 * | 11/2015 | Barton | B65D 75/008 |
| 2002/0130059 | A1 * | 9/2002 | Armijo | A61M 25/002 206/438 |
| 2005/0038453 | A1 | 2/2005 | Raulerson | |
| 2005/0043715 | A1 * | 2/2005 | Nestenborg | A61M 25/002 604/544 |
| 2005/0252805 | A1 * | 11/2005 | Cervantes | A61F 2/0095 206/384 |
| 2007/0228073 | A1 * | 10/2007 | Mazzarino | B65D 75/5811 222/107 |
| 2009/0008279 | A1 * | 1/2009 | Tanghoej | A61M 25/002 206/364 |
| 2009/0306603 | A1 | 12/2009 | Bierman et al. | |
| 2011/0272421 | A1 * | 11/2011 | Barton | B65D 75/366 220/694 |
| 2012/0305441 | A1 * | 12/2012 | Murray | A61M 25/002 206/570 |
| 2014/0110279 | A1 * | 4/2014 | Kruetzfeldt | A61F 2/2427 206/216 |
| 2015/0068939 | A1 | 3/2015 | Seitz, III | |

FOREIGN PATENT DOCUMENTS

| | | |
|---|---|---|
| EP | 2468346 A1 | 6/2012 |
| EP | 2609955 A1 | 7/2013 |
| EP | 2609956 A1 | 7/2013 |
| JP | 2011139882 A | 7/2011 |
| WO | 2002/47602 A2 | 6/2002 |
| WO | WO0247602 A2 | 6/2002 |
| WO | 2005/092419 A1 | 10/2005 |
| WO | WO2005092419 A1 | 10/2005 |
| WO | 2012/079590 A1 | 6/2012 |
| WO | 2015/047455 A2 | 4/2015 |
| WO | 2015/089189 A2 | 6/2015 |
| WO | 2015/089197 A2 | 6/2015 |

OTHER PUBLICATIONS

PCT International Search Report corresponding to International Application No. PCT/US2017/040587; dated Sep. 29, 2017, 13 pages.

PCT/US2017/040587, The International Search Report and the Written Opinion of the International Searching Authority, dated Sep. 29, 2017, 13 pages.

PCT/US2017/040590, The International Search Report and the Written Opinion of the International Searching Authority, dated Sep. 29, 2017, 15 pages.

U.S. Appl. No. 62/359,049, of Jeffrey Barnell, titled "Hybrid Sealed Tray for Long Catheter Delivery Systems", filed Jul. 6, 2016.

U.S. Appl. No. 15/277,509, of Jeffrey Barnell, titled "Hybrid Sealed Tray for Long Catheter Delivery Systems", filed Sep. 27, 2016.

U.S. Appl. No. 15/332,968, of Jeffrey Barnell et al., titled "Device Retention Mechanism and Method", filed Oct. 24, 2016.

U.S. Appl. No. 15/333,287, of John Gallagher, titled "Hinged Long Sealed Tray and Method", filed Oct. 25, 2016.

U.S. Appl. No. 15/333,317, of John Gallagher et al., titled "Slip Card for Long Sealed Trays and Method", filed Oct. 25, 2016.

* cited by examiner

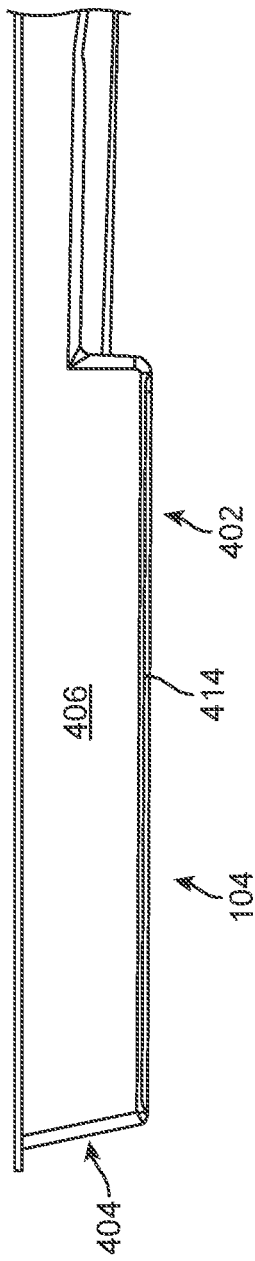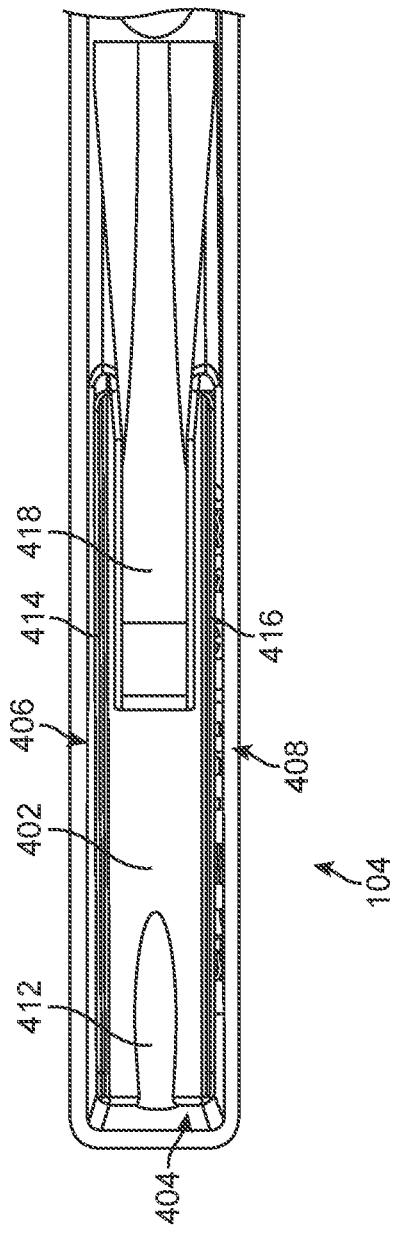

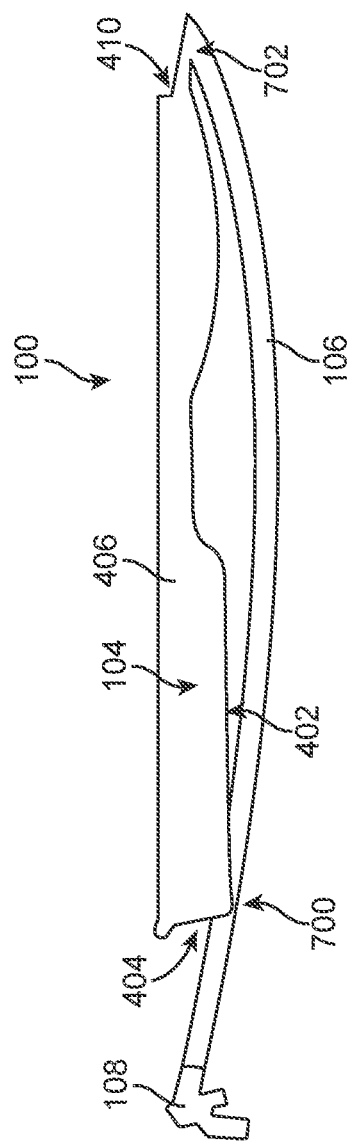
FIG. 7
FIG. 8
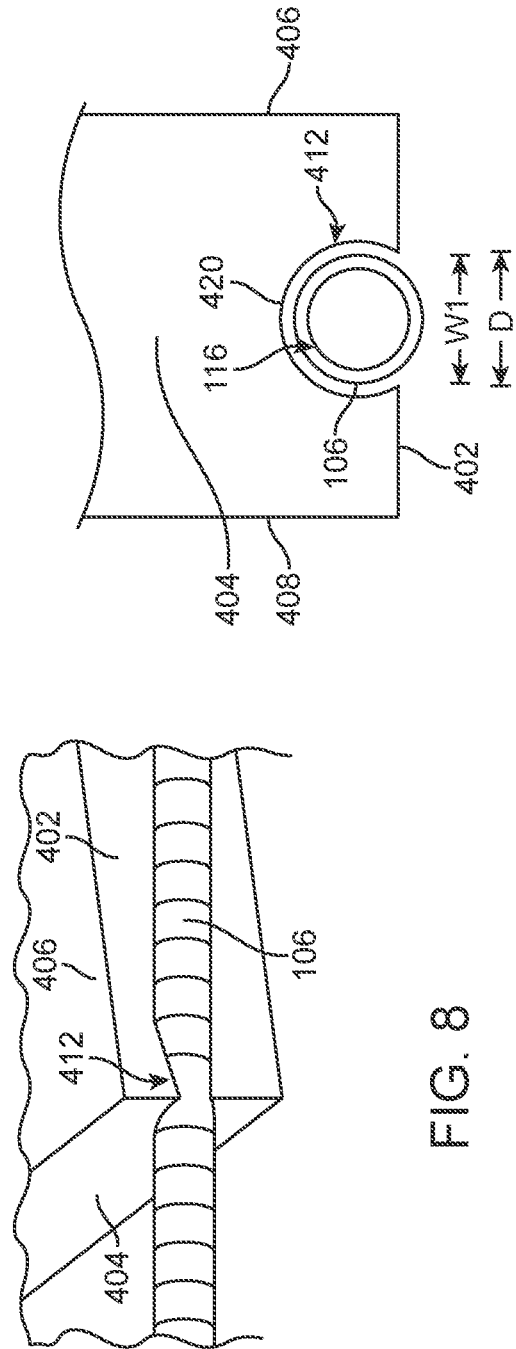
FIG. 9

BIOMATTER CAPTURE MECHANISM AND METHOD

RELATED APPLICATIONS

This application claims the benefit of U.S. Provisional Application No. 62/359,049 filed on Jul. 6, 2016, entitled "HYBRID SEALED TRAY FOR LONG CATHETER DELIVERY SYSTEMS" of Jeffery Barnell, which is incorporated herein by reference in its entirety.

BACKGROUND

Field

The present application relates to packaging for an intra-vascular device and method. More particularly, the present application relates to packaging for a device for treatment of intra-vascular diseases and related methods.

Description of the Related Art

Delivery systems are used to implant one or more endoluminal devices within a patient. During the procedure, biomatter, e.g., blood, is introduced into the delivery system. After the procedure, the delivery system including biomatter is disposed of in a safe manner. Typically, the delivery system is placed into a bio-waste disposal bag in a bio-waste container. However, the delivery system is often long and may puncture the bio-waste disposal bag.

SUMMARY

In accordance with one embodiment, a method of capturing biomatter includes placing a device comprising the biomatter within an extension tube, the extension tube being coupled to a tray. A fold is created in the extension tube sealing the extension tube and the biomatter contained therein. The extension tube is secured to the tray to maintain the fold. The assembly is discarded, e.g., into a bio-waste disposal bag in a bio-waste container. The fold is a smooth fold, in contrast to a sharp tip, thus minimizing the possibility of puncture of the bio-waste disposal bag.

These and other features in accordance with various embodiments will be more readily apparent from the detailed description set forth below taken in conjunction with the accompanying drawings.

BRIEF DESCRIPTION OF DRAWINGS

FIG. 4 is a side plan view of a tray of the catheter delivery system and biomatter capture package of FIGS. 1-2 in accordance with one embodiment.

FIG. 5 is a bottom plan view of the tray of FIG. 4 in accordance with one embodiment.

FIG. 7 is side plan view of a biomatter capture mechanism of the catheter delivery system and biomatter capture package of FIGS. 1-2 in a secured position in accordance with one embodiment.

FIG. 8 is a bottom perspective view of the biomatter capture mechanism of FIG. 7 in accordance with one embodiment.

FIG. 9 is a proximal end cross-sectional view of the biomatter capture mechanism of FIG. 7 in accordance one embodiment.

Common reference numerals are used throughout the drawings and detailed description to indicate like elements.

DETAILED DESCRIPTION

Figure 1:
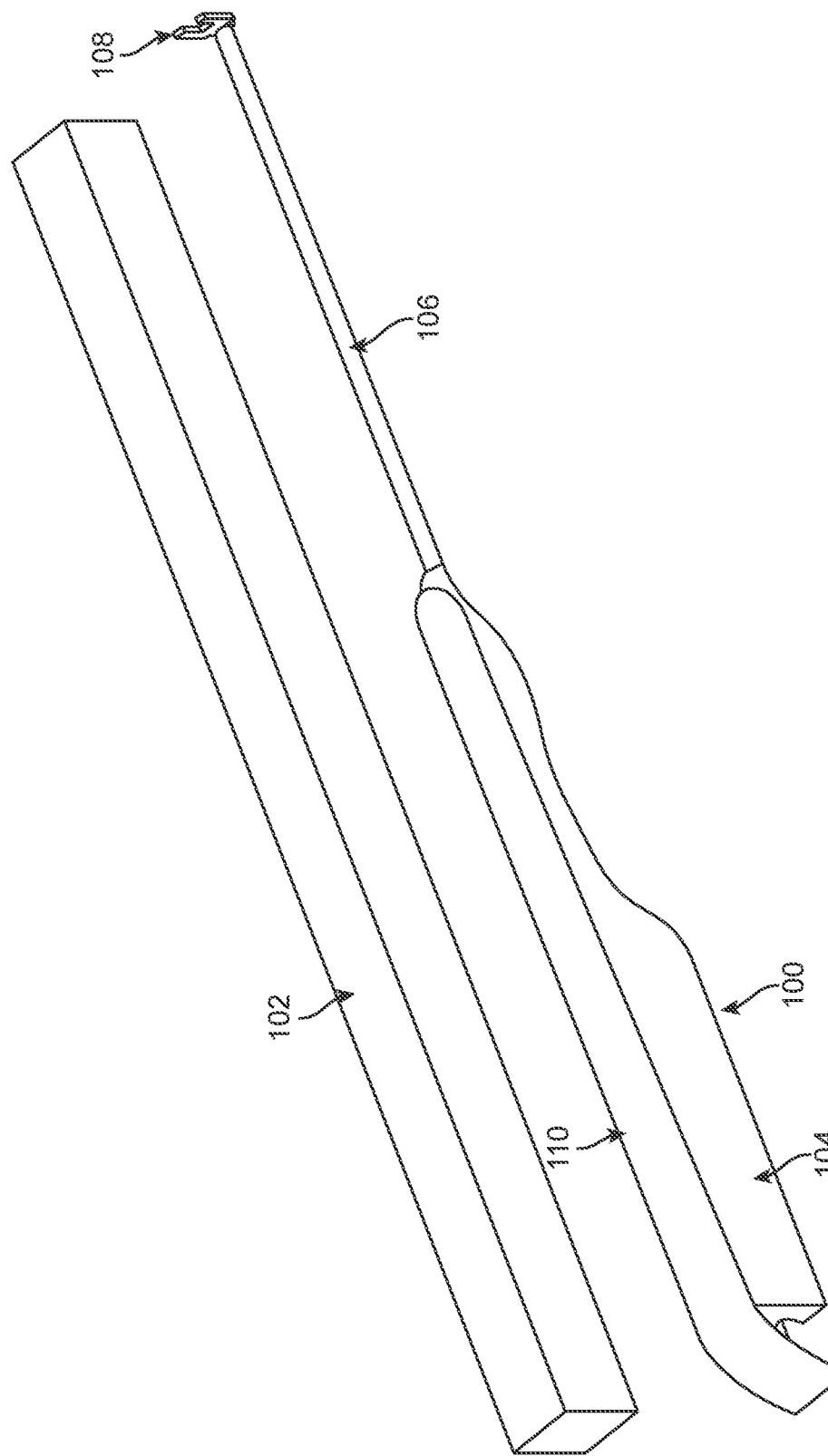
FIG. 1 is a perspective view of a catheter delivery system and biomatter capture package and a shelf carton in accordance with one embodiment.

FIG. 1 is a perspective view of a catheter delivery system and biomatter capture package 100 and a shelf carton 102, sometimes called a box, in accordance with one embodiment. Catheter delivery system and biomatter capture package 100 comes in shelf carton 102, e.g., during transportation from the manufacturer to the medical facility. Catheter delivery system and biomatter capture package 100 includes a biomatter capture mechanism as discussed below.

Figure 2:
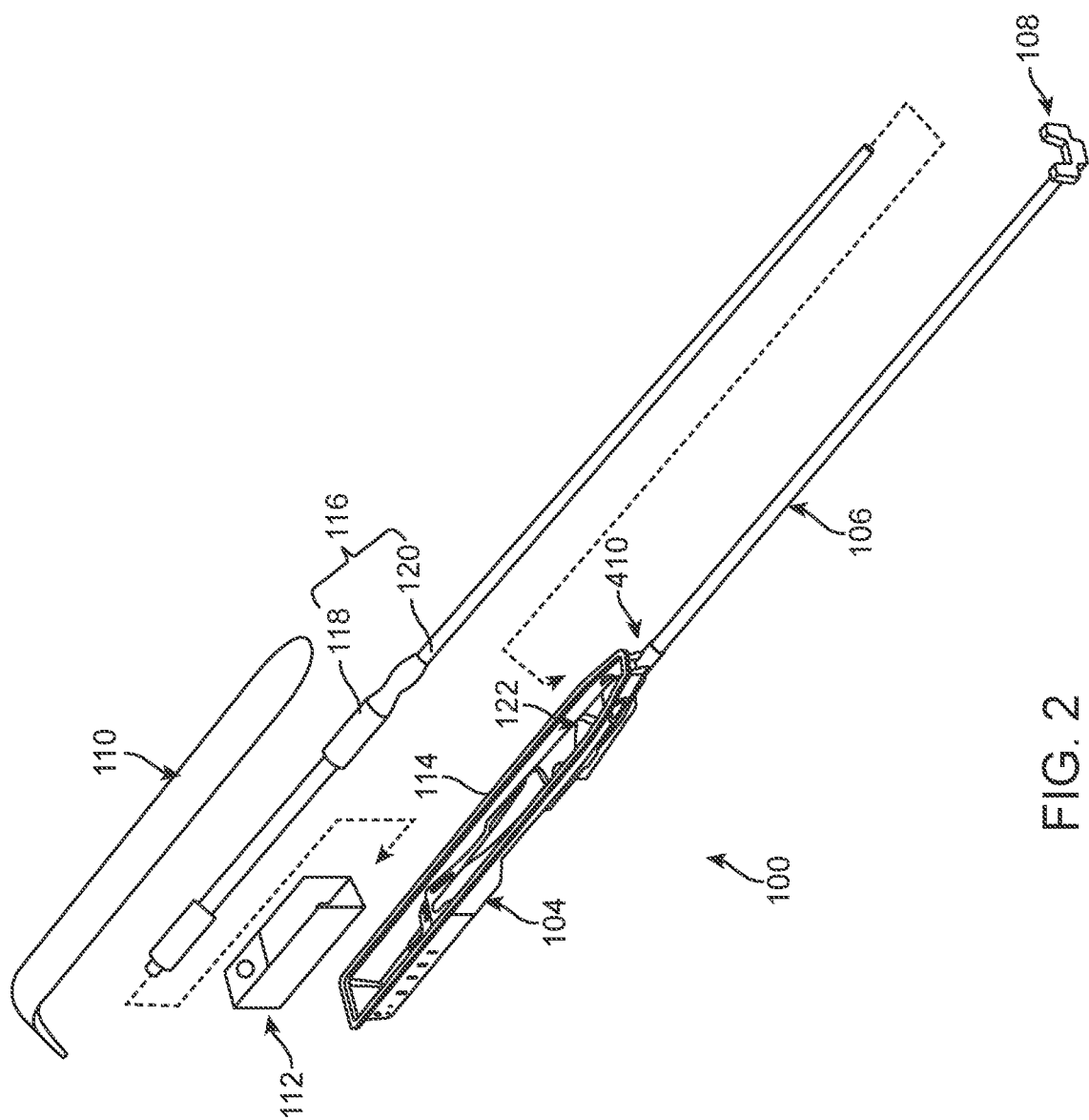
FIG. 2 is an exploded perspective view of the catheter delivery system and biomatter capture package of FIG. 1 in accordance with one embodiment.

FIG. 2 is an exploded perspective view of catheter delivery system and biomatter capture package 100 of FIG. 1 in accordance with one embodiment. Referring to FIGS. 1 and 2 together, catheter delivery system and biomatter capture package 100 includes a tray 104, an extension tube 106, an end cap 108, a lid 110, and a device removal assist card 112. Tray 104, sometimes called a common injection-molded body, is a hybrid sealed tray for long catheter delivery systems. Tray 104 includes an integral lid sealing flange 114 for sealing with lid 110.

Catheter delivery system and biomatter capture package 100 is a sterile package for a delivery system 116. Delivery system 116 include a handle 118 and a protruding portion 120 protruding from handle 118. Examples of delivery system 116 include the Valiant™ Aortic Stent Graft System and the Micra™ Transcatheter Pacing System (TPS) although other delivery systems are used in other embodiments.

In one embodiment, delivery system 116 includes one or more stents, grafts, stent-grafts, or other endoluminal devices for delivery and implantation within a patient. Protruding portion 120, e.g., a delivery system catheter, is cylindrical in accordance with one embodiment and is configured to be inserted into a patient. Protruding portion 120 is not limited to a cylindrical member and can take various shapes and have various features in accordance with other embodiments. Tray 104 constrains handle 118 of delivery system 116 therein while extension tube 106 constrains protruding portion 120 therein.

In various embodiments, tray 104 is formed using injection molding, blow molding, or thermoformed. Hermetically welded to tray 104 is extension tube 106, sometimes called a retention tube. Extension tube 106 is a simple, cylindrical, extruded tube although is injection molded in one embodiment. Extension tube 106 is sized for the length of the protruding portion 120, e.g., the catheter, longer for thoracic and shorter for abdominal devices. Extension tube 106 is a closed profile such as a cylinder, an octagon, an oval, or a square in other embodiments. Extension tube 106 can taper end to end and/or include other functional features along its length, e.g., depending upon the application.

The proximal end of extension tube 106 is coupled to tray 104. End cap 108 hermetically seals the distal end of extension tube 106. In another, embodiment, the distal end of extension tube 106 is directly hermetically sealed, e.g., crimped and melted shut, and end cap 108 is not used in accordance with this embodiment. Generally, the proximal end of extension tube 106 is coupled to tray 104 and a foldable portion of extension tube 106 extends distally from the proximal end to the distal end of extension tube 106, which is sealed, either directly or with end cap 108. High Density PolyEthylene (HDPE) or another resin is used for each component including extension tube 106 enabling reliable welding and recyclability.

After delivery system 116 is placed in tray 104 and extension tube 106, the sterile barrier is created with the additional of lid 110, e.g., a sealed Tyvek lid. The sealing operation takes place on an industry-standard sealer, e.g., a thermal sealer, in one embodiment.

More particularly, a cavity 122 is defined by tray 104, extension tube 106, and lid 110. Delivery system 116 is contained within cavity 122 in a sterile condition.

To remove and use delivery system 116, lid 110 is removed. Handle 118 is removed from tray 104, e.g., with the assistance of device removal assist card 112. Protruding portion 120 of delivery system 116 is removed from extension tube 106. Protruding portion 120 of delivery system 116 is then inserted into a patient, e.g., to implant one or more and endoluminal devices within the patient. During this procedure, biomatter, e.g., blood, is introduced into delivery system 116.

Figure 3:
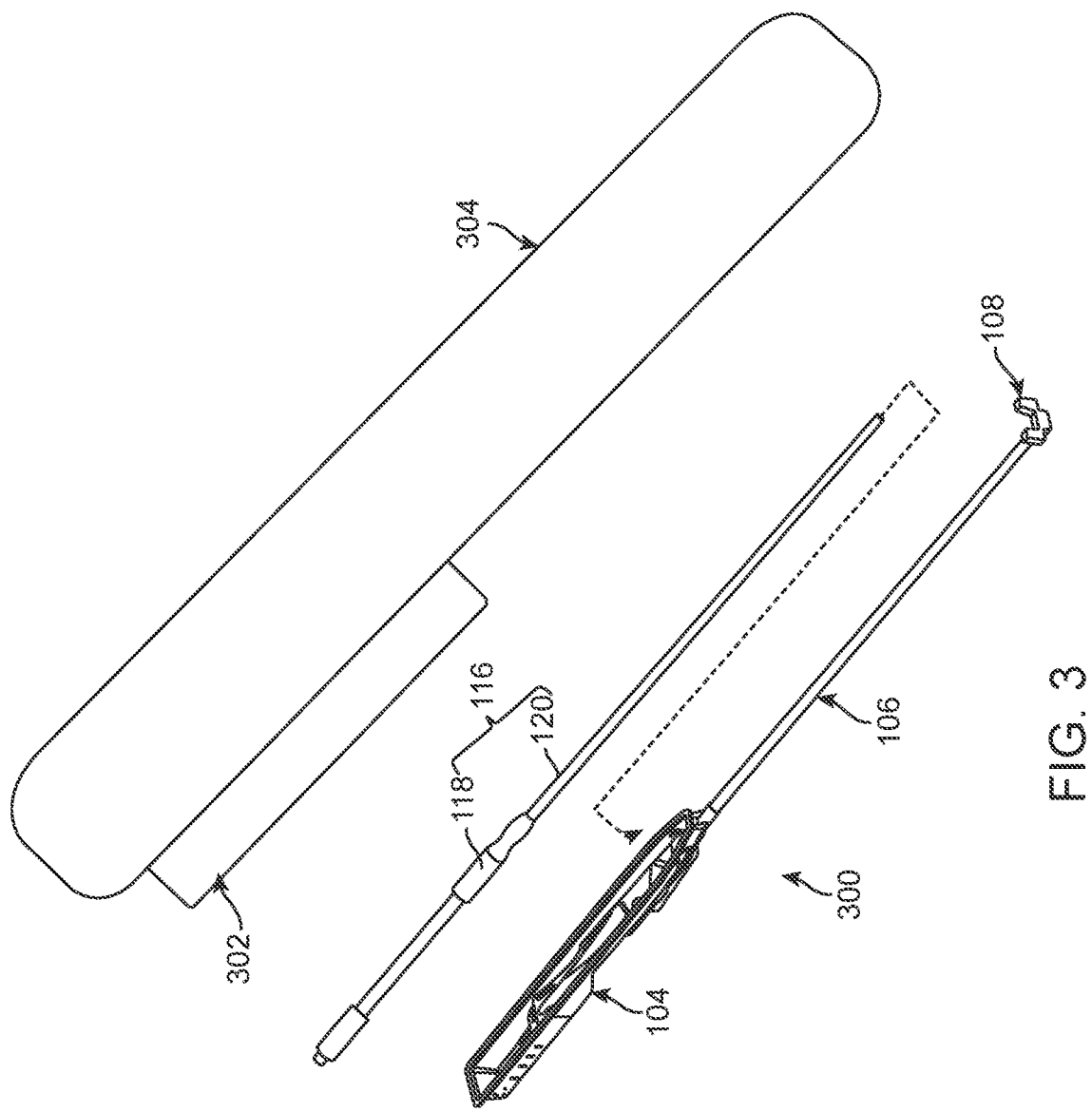
FIG. 3 is an exploded perspective view of a catheter delivery system and biomatter capture package in accordance with another embodiment.

FIG. 3 is an exploded perspective view of a catheter delivery system and biomatter capture package 300 in accordance with another embodiment. Catheter delivery system and biomatter capture package 300 of FIG. 3 is similar to catheter delivery system and biomatter capture package 100 of FIGS. 1-2 and only the significant differences are discussed below.

In accordance with this embodiment, tray 104 including handle 118 are contained in a sterile condition within an inner bag 302. The entire assembly including tray 104, extension tube 106, end cap 108, delivery system 116, and inner bag 302 are contained within an outer bag 304.

To remove and use delivery system 116, tray 104, extension tube 106, end cap 108, delivery system 116, and inner bag 302 are removed from outer bag 304. Inner bag 302 is then removed to expose handle 118. Handle 118 is removed from tray 104 while also removing protruding portion 120 from extension tube 106. Protruding portion 120 of delivery system 116 is then inserted into a patient, e.g., to implant one or more and endoluminal devices within the patient. During this procedure, biomatter, e.g., blood, is introduced into delivery system 116.

Although a particular tray 104 is illustrated in FIGS. 1-3, in accordance with other embodiments, tray 104 can take a wide variety of shapes and sizes, e.g., be an open tray, depending upon the particular application.

In the following description, tray 104, extension tube 106, end cap 108, and delivery system 116 of catheter delivery system and biomatter capture package 100 of FIGS. 1-2 are discussed. However, in light of this disclosure, those of skill in the art will understand that the following description is equally applicable to tray 104, extension tube 106, end cap 108, and delivery system 116 of catheter delivery system and biomatter capture package 300 of FIG. 3.

Figure 6:
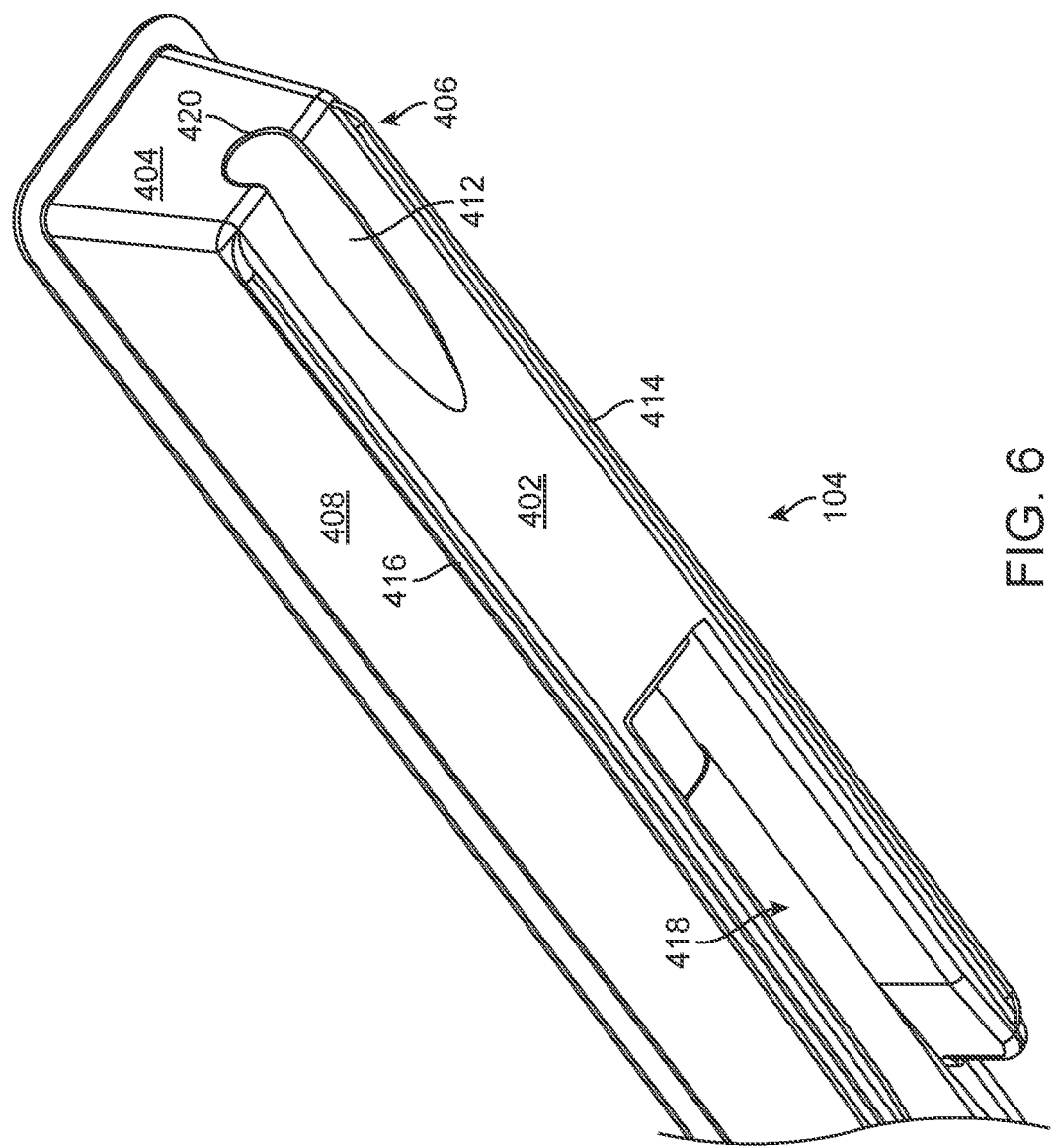
FIG. 6 is a bottom perspective view of the tray of FIG. 4 in accordance with one embodiment.

FIG. 4 is a side plan view of tray 104 of catheter delivery system and biomatter capture package 100 of FIGS. 1-2 in accordance with one embodiment. FIG. 5 is a bottom plan view of tray 104 of FIG. 4 in accordance with one embodiment. FIG. 6 is a bottom perspective view of tray 104 of FIG. 4 in accordance with one embodiment.

Referring now to FIGS. 1-2, 4-6 together, tray 104 includes a bottom surface 402, a proximal end 404, sides 406, 408, and a distal end 410. Extension tube 106 is coupled to distal end 410 of tray 104. Sides 406, 408 and ends 404, 410 extend upward and away from bottom surface 402. Sides 406, 408 extend opposite one another and between proximal end 404 and distal end 410. Similarly, proximal end 404 and distal end 410 extend opposite one another and between sides 406, 406.

As used herein, the distal end of delivery system 116 is identified as the end that is farthest from the operator (handle 118) while the proximal end of delivery system 116 is the end nearest the operator (handle 118). Similarly, the distal end of catheter delivery system and biomatter capture package 100 is identified to the end that is farthest from tray 104 (handle 118) while the proximal end of catheter delivery system and biomatter capture package 100 is the end nearest tray 104 (handle 118).

Bottom surface 402, and generally tray 104, includes a tube slot 412, end cap rails 414, 416, and an end cap slot 418 therein in accordance with this embodiment. Although tray 104 is illustrated and discussed as including tube slot 412, end cap rails 414, 416, and end cap slot 418, in other embodiments, tray 104 includes one or more of tube slot 412, end cap rails 414, 416, and end cap slot 418.

Paying particular attention to tube slot 412, tube slot 412 is a curved surface extending from proximal end 404 towards distal end 410 of tray 104. Tube slot 412 forms a partially circular tube slot opening 420 in proximal end 404 and then tapers in depth from proximal end 404 to exit bottom surface 402. In one embodiment, tube slot 412 has a shape defined as a cylindrical surface cut by the plane of bottom surface 402. Tube slot opening 420 is sometimes called a major arc as the circumference of opening 420 is an arc larger than a semicircle.

FIG. 7 is side plan view of a biomatter capture mechanism 700 of catheter delivery system and biomatter capture package 100 of FIGS. 1-2 in a secured position in accordance with one embodiment. FIG. 8 is a bottom perspective view of biomatter capture mechanism 700 of FIG. 7 in accordance with one embodiment. FIG. 9 is a proximal end cross-sectional view of biomatter capture mechanism 700 of FIG. 7 in accordance one embodiment. Referring now to FIGS. 1-2, 4-9 together, biomatter capture mechanism 700 includes extension tube 106 in combination with tube slot 412.

More particularly, after the patient procedure, e.g., deployment of a device from delivery system 116, delivery system 116 including trapped biomatter, e.g., blood, is placed back into catheter delivery system and biomatter capture package 100. Specifically, protruding portion 120 is placed into extension tube 106, which is foldable. Extension tube 106 is then folded as illustrated in FIG. 7. This creates a fold 702 in extension tube 106 that pinches shut, i.e., seals, extension tube 106 at fold 702. This traps biomatter within extension tube 106.

For longer extension tubes 106, e.g., thoracic length, extension tube 106 is folded until extension tube 106 is locked into tube slot 412. Tube slot 412 is shaped such that extension tube 106 snaps or is otherwise secured therein. For example, as shown in FIG. 9, a width W1 of tube slot 412 at an intersection of proximal end 404 and bottom surface 402 is less than a diameter D of extension tube 106 such than extension tube 106 must be compressed to pass into tube slot 412 and is then secured therein.

After extension tube 106 is placed into tube slot 412, the assembly is discarded, e.g., into a bio-waste disposal bag in a bio-waste container. Fold 702 is a smooth fold, in contrast to a sharp tip, thus minimizing the possibility of puncture of the bio-waste disposal bag.

Figure 10:
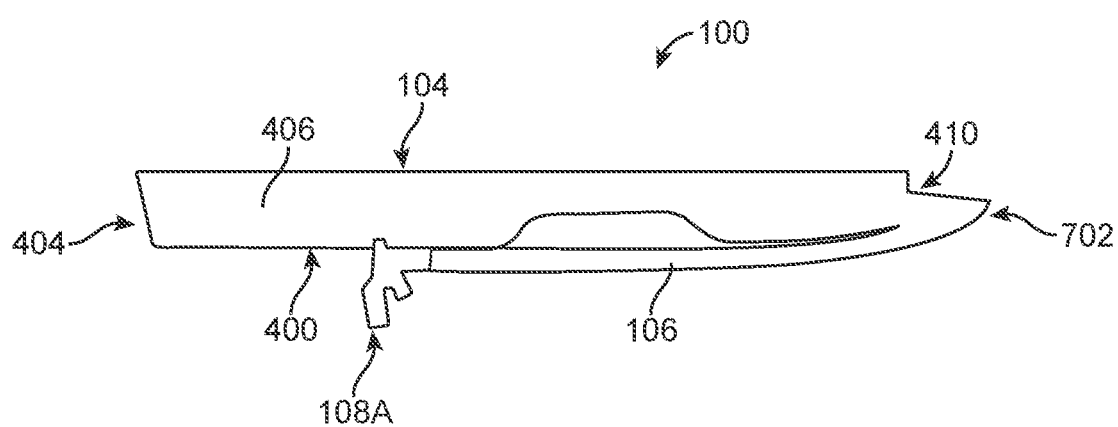
FIG. 10 is side plan view of a biomatter capture mechanism of the catheter delivery system and biomatter capture package of FIGS. 1-2 in a secured position in accordance with another embodiment.
Figure 11:
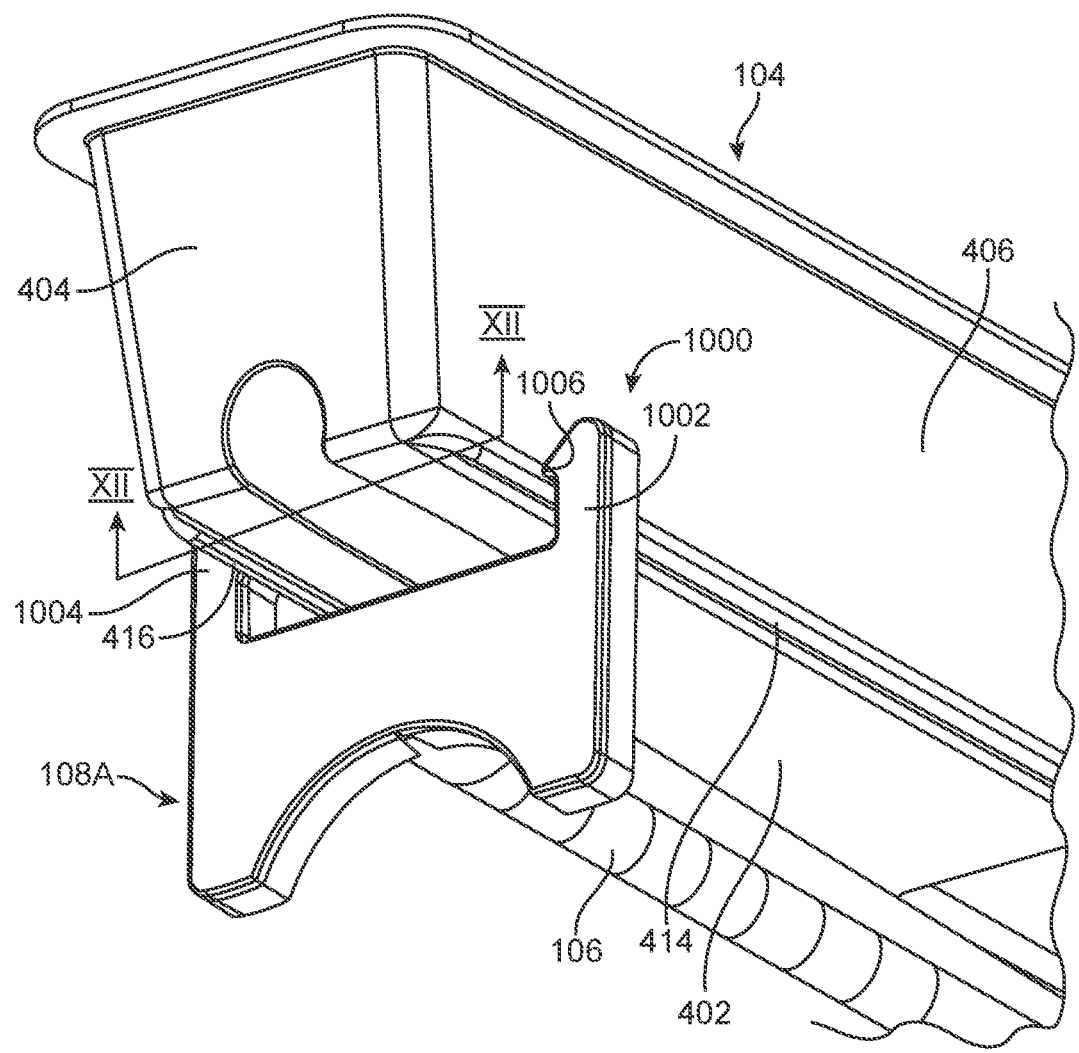
FIG. 11 is a bottom perspective view of the biomatter capture mechanism of FIG. 10 in accordance with one embodiment.
Figure 12:
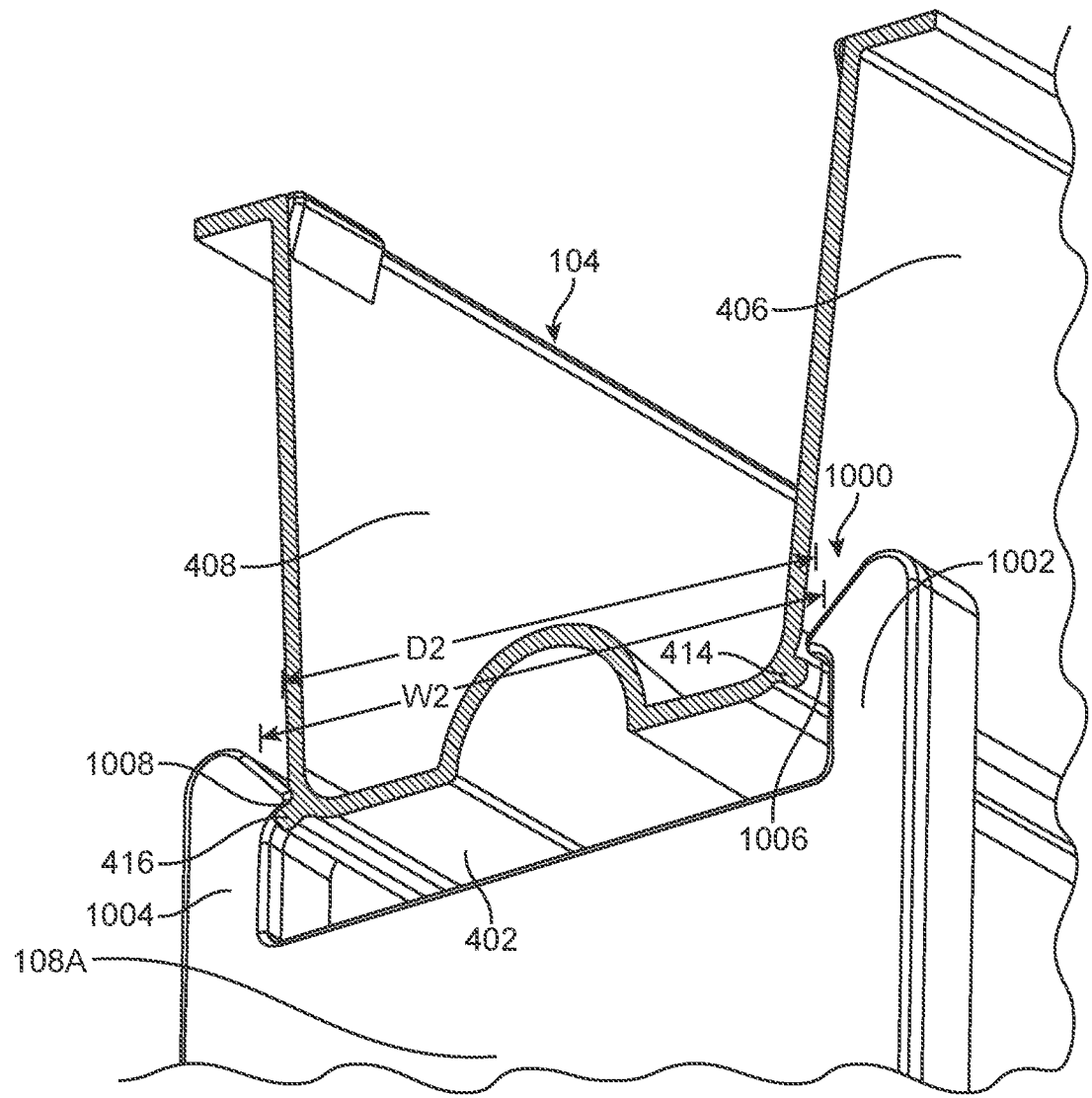
FIG. 12 is a cross-sectional view of the biomatter capture mechanism along the line XII-XII of FIG. 11 in accordance one embodiment.

FIG. 10 is side plan view of a biomatter capture mechanism 1000 of catheter delivery system and biomatter capture package 100 of FIGS. 1-2 in a secured position in accordance with another embodiment. FIG. 11 is a bottom perspective view of biomatter capture mechanism 1000 of FIG. 10 in accordance with one embodiment. FIG. 12 is a cross-sectional view of biomatter capture mechanism 1000 along the line XII-XII of FIG. 11 in accordance one embodiment. Referring now to FIGS. 1-2, 10-12 together, biomatter capture mechanism 1000 includes extension tube 106 in combination with an end cap 108A and end cap rails 414, 416.

More particularly, after the patient procedure, e.g., deployment of a device from delivery system 116, delivery system 116 including trapped biomatter, e.g., blood, is placed back into catheter delivery system and biomatter capture package 100. Specifically, protruding portion 120 is placed into extension tube 106, which is foldable. Extension tube 106 is then folded, sometimes called bent, as illustrated in FIG. 10. This creates a fold 702 in extension tube 106 that pinches shut, i.e., seals, extension tube 106 at fold 702. This traps biomatter within extension tube 106.

For shorter extension tubes 106, e.g., abdominal length, extension tube 106 is folded until end cap 108A is snapped and locked to end cap rails 414, 416. End cap rails 414, 416 are linear rails protruding from bottom surface 402 at sides 406, 408, respectively. A width W2 between end cap rails 414, 416 exists.

End cap 108A includes opposing clasps 1002, 1004 protruding from end cap 108A in a direction perpendicular to a longitudinal axis of extension tube 106. Clasps 1002, 1004 are snapped around end cap rails 414, 416. More particularly, clasps 1002, 1004 include pointed tips 1006, 1008, that point inward at one another. A distance D2 between tips 1006, 1008 is less than width W2 of end cap rails 414, 416. Accordingly, end cap 108A is pressed against rails 414, 416, which causes tips 1006, 1008 to spread around rails 414, 416 and then snap back together around rails 414, 416. This engages clasps 1002, 1004 to end cap rails 414, 416. Generally, this secures end cap 108A to tray 104.

End cap rails 414, 416 are linear rails accommodating variation in the placement of end cap 108A. More particularly, end cap 108A can be snapped to end cap rails 414, 416 anywhere along the length of end cap rails 414, 416 providing a large landing pad for end cap 108A. Accordingly, end cap rails 414, 416 along with end cap 108A accommodate variations in the length of extension tube 106 along with variation in where fold 702 is created.

After end cap 108A is snapped to end cap rails 414, 416, the assembly is discarded, e.g., into a bio-waste disposal bag in a bio-waste container. Fold 702 is a smooth fold, in contrast to a sharp tip, thus minimizing the possibility of puncture of the bio-waste disposal bag.

Figure 13:
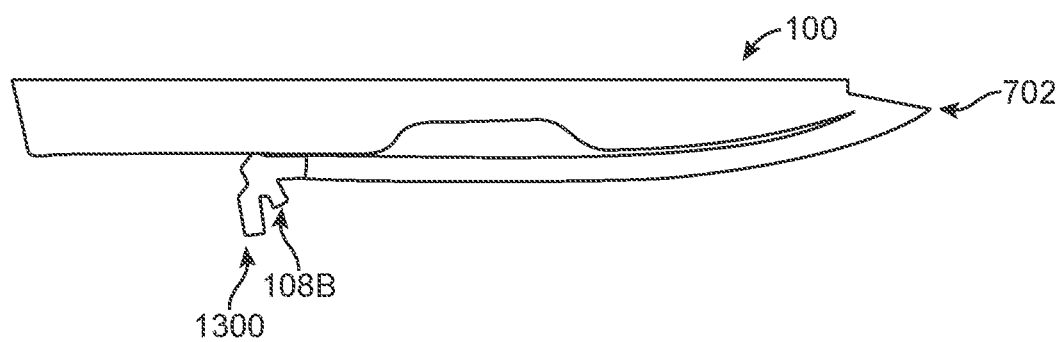
FIG. 13 is side plan view of a biomatter capture mechanism of the catheter delivery system and biomatter capture package of FIGS. 1-2 in a secured position in accordance with another embodiment.
Figure 14:
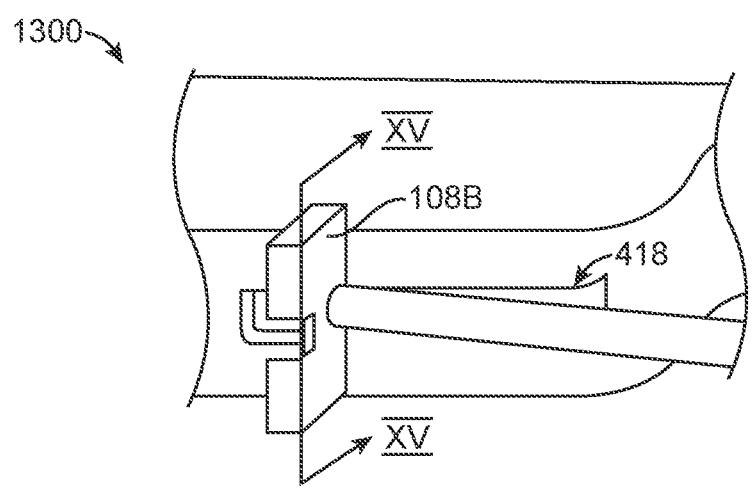
FIG. 14 is a bottom perspective view of the biomatter capture mechanism of FIG. 13 in accordance with one embodiment.
Figure 15:
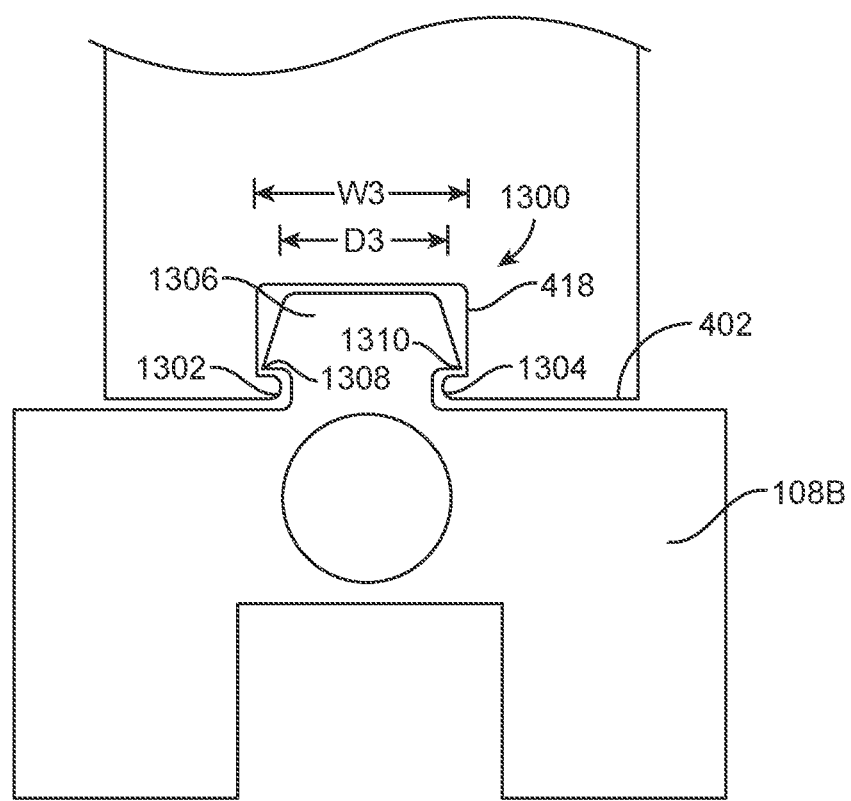
FIG. 15 is a cross-sectional view of the biomatter capture mechanism along the line XV-XV of FIG. 14 in accordance one embodiment.

FIG. 13 is side plan view of a biomatter capture mechanism 1300 of catheter delivery system and biomatter capture package 100 of FIGS. 1-2 in a secured position in accordance with another embodiment. FIG. 14 is a bottom perspective view of biomatter capture mechanism 1300 of FIG. 13 in accordance with one embodiment. FIG. 15 is a cross-sectional view of biomatter capture mechanism 1300 along the line XV-XV of FIG. 14 in accordance one embodiment. Referring now to FIGS. 1-2, 13-15 together, biomatter capture mechanism 1300 includes extension tube 106 in combination with an end cap 108B and end cap slot 418.

More particularly, after the patient procedure, e.g., deployment of a device from delivery system 116, delivery system 116 including trapped biomatter, e.g., blood, is placed back into catheter delivery system and biomatter capture package 100. Specifically, protruding portion 120 is placed into extension tube 106, which is foldable. Extension tube 106 is then folded as illustrated in FIG. 13. This creates a fold 702 in extension tube 106 that pinches shut, i.e., seals, extension tube 106 at fold 702. This traps biomatter within extension tube 106.

For shorter extension tubes 106, e.g., abdominal length, extension tube 106 is folded until end cap 108B is snapped and locked to end cap slot 418. End cap slot 418 includes end cap rails 1302, 1304 protruding inward and towards one another at bottom surface 402. A distance D3 between end cap rails 1302, 1304 exists.

End cap 108B includes a tab 1306 protruding from end cap 108B in a direction perpendicular to a longitudinal axis of extension tube 106. Tab 1306 is snapped into end cap slot 418. More particularly, tab 1306 includes pointed tips 1308, 1310 that point outward away from one another. A width W3 between tips 1308, 1310 is greater than distance D3 between end cap rails 1302, 1304. Accordingly, end cap 108B is pressed into end cap slot 418, which causes tips 1308, 1310 to compress between end cap rails 1302, 1304 and then snap back outward inside of end cap rails 1302, 1304. This secures end cap 108B to tray 104.

After end cap 108B is snapped inside of end cap slot 418, the assembly is discarded, e.g., into a bio-waste disposal bag in a bio-waste container. Fold 702 is a smooth fold, in contrast to a sharp tip, thus minimizing the possibility of puncture of the bio-waste disposal bag.

Although various examples of attachment structures for attaching folded extension tube 106 to tray 104 are set forth above, in other embodiments, end cap 108 and/or extension tube 106 are attached to tray 104 using other attachment structures. Generally, a folded extension tube is attached to a tray using an attachment structure.

These attachment structures include an end cap that snaps to a tray. Illustratively, the end cap snaps into a slot, along rails, in a groove and/or to a protrusion.

In another embodiment, the end cap includes a projecting molded part, e.g., a mushroom shaped projection, molded into the end cap that snaps into a corresponding opening molded into a bottom of the tray. For example, referring to FIG. 15, in one embodiment, the cross-sectional profile of tab 1306 is illustrative of a cross-sectional profile of a mushroom shaped projection of the end cap, and the corresponding opening, e.g., a circular opening, of the tray has a cross-sectional profile similar to the cross-sectional profile of end cap slot 418 as illustrated in FIG. 15. However, in other embodiments, the projecting molded part of the end cap and the corresponding opening in the tray have other corresponding snapping shapes. In yet another embodiment, the tray includes a projecting molded part and the end cap includes a corresponding opening In another embodiment, an adhesive strip mounts the folded extension tube to the tray directly by coupling the folded extension tube to the tray or indirectly, e.g., by coupling the end cap to the tray.

In another embodiment, the attachment structure includes a snap fastener, sometimes called a button design, that attaches the folded extension tube, either directly or indirectly, e.g., by the end cap, to the tray. In one embodiment, a snap fastener includes a pair of interlocking discs that snap together. For example, a circular lip under one disc fits into groove on the top of the other disc.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A biomatter capture mechanism comprising:
   an extension tube, the extension tube having a closed profile and a hermetically sealed distal end;
   a tray, a proximal end of the extension tube being permanently coupled to a distal end of the tray, the extension tube being foldable, wherein the extension tube is configured to be attached to the tray when folded; and
   a curved slot at a proximal end of the tray, the curved slot being configured to receive and secure the extension tube therein;
   wherein when the extension tube is folded it is secured in the curved slot such that the hermetically sealed distal end extends proximally past the proximal end of the tray.

2. The biomatter capture mechanism of claim 1 wherein the extension tube consists of a cylindrical tube.

3. The biomatter capture mechanism of claim 1 wherein the extension tube comprises a resin.

4. The biomatter capture mechanism of claim 1 further comprising biomatter within the extension tube.

5. The biomatter capture mechanism of claim 4 wherein the extension tube comprises a fold therein.

6. The biomatter capture mechanism of claim 5 wherein the extension tube is snapped to the tray.

7. The biomatter capture mechanism of claim 5 wherein the fold seals the extension tube.

8. The biomatter capture mechanism of claim 5 wherein the fold pinches shut the extension tube.

9. The biomatter capture mechanism of claim 1 wherein the extension tube is hermetically welded to the tray.

10. The biomatter capture mechanism of claim 1 wherein the tray comprises a lid sealing flange.

11. The biomatter capture mechanism of claim 10 further comprising a lid sealed to the lid sealing flange.

12. The biomatter capture mechanism of claim 1 wherein the proximal end of the extension tube is directly coupled to the distal end of the tray.

13. A biomatter capture mechanism comprising:
    an extension tube, the extension tube having a closed profile and a hermetically sealed distal end;
    a tray, a proximal end of the extension tube being permanently coupled to a distal end of the tray, the extension tube being foldable, wherein the extension tube is configured to be attached to the tray when folded; and
    a slot at a proximal end of the tray, the slot being configured to receive the extension tube therein, wherein the slot tapers from the proximal end of the tray.

14. The biomatter capture mechanism of claim 13 further comprising:
    an end cap coupled to the distal end of the extension tube, the end cap being configured to engage the tray.

15. The biomatter capture mechanism of claim 14 wherein the end cap comprises end cap rails comprising clasps, the clasps being configured to engage end cap rails of the tray.

16. The biomatter capture mechanism of claim 14 wherein the extension tube comprises a fold therein, the fold sealing the extension tube, and wherein the end cap is secured to the tray.

17. The biomatter capture mechanism of claim 13 wherein the tray further comprises a bottom surface, the distal end and the proximal end of the tray extending upward and away from the bottom surface, the bottom surface comprising the slot.

* * * * *